United States Patent
Wang et al.

(10) Patent No.: US 7,983,853 B2
(45) Date of Patent: Jul. 19, 2011

(54) EIT DATA PROCESSING SYSTEM AND METHOD

(75) Inventors: Mi Wang, Cheadle (GB); Yunfeng Dai, Beijing (CN); Yixin Ma, Tianjin (CN); Nigel Thomas Holliday, Winchester (GB)

(73) Assignee: University of Leeds, Leeds (GB)

( * ) Notice: Subject to any disclaimer, the term of this patent is extended or adjusted under 35 U.S.C. 154(b) by 1279 days.

(21) Appl. No.: 10/570,054

(22) PCT Filed: Aug. 27, 2004

(86) PCT No.: PCT/GB2004/003670
§ 371 (c)(1), (2), (4) Date: Oct. 17, 2006

(87) PCT Pub. No.: WO2005/022138
PCT Pub. Date: Mar. 10, 2005

(65) Prior Publication Data
US 2007/0166011 A1     Jul. 19, 2007

(30) Foreign Application Priority Data

Aug. 28, 2003 (GB) .................................. 0320167.0

(51) Int. Cl.
*A61B 5/05* (2006.01)
(52) U.S. Cl. .............................. 702/40; 600/425
(58) Field of Classification Search .............. 702/40; 378/21
See application file for complete search history.

(56) References Cited

U.S. PATENT DOCUMENTS

| | | | | |
|---|---|---|---|---|
| 4,135,247 A | * | 1/1979 | Gordon et al. | 378/11 |
| 4,298,936 A | | 11/1981 | Shapiro | |
| 4,438,488 A | | 3/1984 | Shibayama et al. | |
| 4,486,835 A | * | 12/1984 | Bai et al. | 378/21 |
| 5,311,878 A | | 5/1994 | Brown et al. | |
| 5,417,218 A | * | 5/1995 | Spivey et al. | 600/448 |
| 6,748,044 B2 | * | 6/2004 | Sabol et al. | 378/4 |

OTHER PUBLICATIONS

G. P. Lucas et al., "Measurement of the solids volume fraction and velocity distributions in solids-liquid flows using dual-plane electrical resistance tomography", Flow Measurement and Instrumentation, vol. 10, 1999, pp. 249-258; XP008040707, p. 250, left-hand column, last paragraph—p. 252, left-hand column.
B. S. Hoyle et al., "Design and application of a multi-modal process tomography system" Measurement Science and Technology, vol. 12, 2001, pp. 1157-1165; XP008040617 abstract.
M. Wang et al. "Characterization of gas-water flow using electrical resistance imaging" 11$^{th}$ International Conference on Multiphase 03, Jun. 13, 2003, pp. 595-604; XP008040620, Italy, p. 598.

* cited by examiner

*Primary Examiner* — Jonathan C Teixeira Moffat
(74) *Attorney, Agent, or Firm* — Sheridan Ross, P.C.

(57) ABSTRACT

Electrical impedance tomography (EIT) data processing system, for acquiring and processing data from two-phase flows, comprising a dual-plane sensor, a plurality of digital signal processing modules configured in a data pipeline processing arrangement and a plurality of data acquisition subsystems in communication with a first one of said digital signal processing modules.

24 Claims, 11 Drawing Sheets

(a) Simplified Schematic (b) Equivalent Schematic (a)          (b)          (c)

(a) Data collected from an air-water flow (SH1) at f=134.2 fps, d=5cm (b) Data collected from an oil-water flow (M4) at f=914.3 fps, d=3cm.

(a)

(b)

EIT DATA PROCESSING SYSTEM AND METHOD

CROSS REFERENCE TO RELATED APPLICATIONS

This application is a national phase patent application of PCT/GB04/03670 filed on Aug. 27, 2004 which claims priority to United Kingdom Patent No. 0320167.0 filed on Aug. 28, 2003.

This invention relates to the field of electrical impedance tomography (EIT), and in particular to EIT data processing systems and methods.

BACKGROUND OF THE INVENTION

There are many industrial two-component flow applications where it is required to monitor the flow rate of one, or both, of the flowing components. In a two component flow where the continuous component is electrically conductive, and where there is a conductivity contrast between the continuous and discontinuous components, a technique known as dual-plane Electrical Impedance Tomography (EIT) has the potential to be used on-line to obtain accurate estimates of the local disperse phase volumetric flow rate, the mean disperse and continuous phase volume fractions and the distributions of the local axial, radial and angular velocity components of the disperse phase.

The invention is concerned with online data acquisition and processing of measurements from two-phase flows, whose axial velocities can be up to $10\ \text{ms}^{-1}$, with ±5% precision. To be able to measure two-phase flows at these velocities requires data acquisition and processing speeds of 1000 frames per second per dual-plane in order to generate flow velocity maps and this has not been possible to date, using conventional techniques.

The following prior art documents are incorporated herein by reference.

DICKIN F, WANG M, *Electrical resistance tomography for process applications*, Meas. Sci. Technol. 7 (1996), 247-260

WANG M, DICKIN F J, BECK M S, *Improved electrical impedance tomography data collection system and measurement protocols*, Tomography Technique and Process Design and Operation ISBN1813122467

TII, (2000), TMA320C6202/B *Fixed-Point Digital Signal Processors*, Texas Instruments Incorporated WANG M., (1994), *Electrical impedance tomography on conducting walled process vessels*, PhD thesis, UMIST

SUMMARY OF THE INVENTION

It is an object of the present invention to provide systems and methods for multiphase flow measuring that are robust, non-invasive and can deliver on-line multi-dimensional flow information.

According to a first aspect of the invention, there is provided an electrical impedance tomography (EIT) data processing system, for acquiring and processing data from two-phase flows, comprising a dual-plane sensor, a plurality of digital signal processing modules configured in a data pipeline processing arrangement and a plurality of data acquisition subsystems in communication with a first one of said digital signal processing modules.

Preferably, the data pipeline processing arrangement is capable of acquiring and/or processing 1000 dual frames per second per dual-plane.

Preferably, said dual-plane sensor comprises an electrode array in communication with one of said data acquisition subsystems.

In a preferred embodiment, said data acquisition subsystems each include one or more of a voltage controlled current source, an equal-width pulse synthesiser, a synchronised digital demodulation unit and an over-zero switch.

The voltage controlled current source preferably comprises a parallel structure of eight AD844 chips or equivalents, configured as four pairs in which the two inverting inputs of each pair are cascaded together with a current-setting resistor. The four negative and four positive current outputs of the AD844 chips are summed together to provide total negative and positive current outputs.

Preferably, the voltage controlled current source further comprises a DC restore facility in which a capacitor and a resistor connected to the non-inverting input of each AD844 chip restore DC components and cancel the DC offset at the current outputs.

In a preferred embodiment, the voltage controlled current source includes a potentiometer for amplitude balancing.

Preferably, said equal-width pulse synthesiser comprises a clock signal for triggering an address generator to continuously output addresses to a pre-programmed memory, the memory output being connected to a digital to analogue converter, the digital to analogue converter providing a staircase signal output, characterised in that different sampling rates are provided at different signal frequencies so that the staircase signal output has the same time step-length at all frequencies.

Preferably, the synchronised digital demodulation unit comprises 16 sets of programmable gain amplifiers each having an analogue to digital converter, a strobed First-In First-Out (FIFO) memory and control logic and wherein the signal output of the equal-width pulse synthesiser triggers said 16 analogue to digital converters to acquire measurement data in parallel at predefined intervals.

Preferably, said over-zero switch comprises two multiplexers, each having 16 electrodes mounted in one sensing plane connected to their 16 output channels and two flip-flops controlled by a switching command from one of said DSP modules and, ideally, a D-type flip-flop for preventing data being written prematurely to the second of said flip-flops.

According to a second aspect of the invention, there is provided a method of acquiring and processing electrical impedance tomography data from two-phase flows using the system as claimed in any of the preceding claims.

According to a third aspect of the invention there is provided a recording medium having recorded thereon computer implementable instructions for performing the method described in the preceding paragraph.

The system has been carefully designed in a modular fashion and can consist of several data acquisition modules and computing modules. The data acquisition modules include a voltage controlled current source with a DC-restore circuit, an equal-width pulse synthesizer unit to produce synthetic waveforms for electric field excitation, synchronized switching, and sampling control, and a synchronized digital demodulation unit consisting of sixteen parallel measurement channels. The computing modules include a powerful digital signal processor (for example TMS320C6202B/6713) with an IEEE1394 communication interface. Several DSP modules can be pipelined for a series of tasks ranging from measurement control to image reconstruction to flow velocity implementation. The DSP system can implement two image reconstruction methods: the single-step SCG method and the back-projection method. An online-updating cross-correlation algorithm has been developed and is to be implemented on the system to calculate flow velocity. This technique is less time and memory consuming compared to direct cross-correlation techniques. The system architecture, detailed modular design, and data processing algorithms are introduced below. With a little optimization on hardware, a speed of data acquisition of 1164 dual-frames (2.383 million data points) per second has been achieved with a root mean square value less than 0.8%@80 kHz using a water phantom.

The very high speed of data acquisition and processing afforded by the system of the present invention is achieved as a result of one or more of the following:

- reducing the time required for multiple-tasks, such as data collection, image reconstruction and flow velocity implementation by the use of the data pipeline process with multi DSP (see FIG. 1);
- the speed of signal coupling due to the transient time of the improved wide bandwidth coupling circuit with differential discharge circuits, therefore significantly reducing the transient time (see the SDD, FIG. 10);
- the residual voltage in capacitance of coupling due to the electric charge being switched at the zero voltage point, or zero charged energy of the capacitance charged by the sinusoidal current, significantly reducing the transient time (shown in the OZS of FIG. 11);
- the data collection operation speed, improved by the parallel structure of the SDD of FIG. 8;
- the time required for transferring and storing data to memory, reduced by the logical controlled FIFO memory (see the SDD and FIGS. 3 and 8);
- the limited sampling speed of the analogue to digital converter limits the application to high frequency in conventional methods but this limitation was overcome in the present system by employing a rolling sampling method (see SDD and FIG. 9d);
- the time limitation of the control operation of the microprocessor, improved by the use of the logical control (not DSP), see SDD and FIG. 8;
- improved data transfer from data acquisition subsystems to DSP to empty FIFO memory for the next operation, realized by the use of a fast DSP-FIFO interface (FIG. 1).

Using the system and method of the present invention, properties of the flow can be measured accurately even when the flow is highly non-uniform. Dual-plane EIT has the added advantage of providing on-line volume fraction and velocity distributions which can be used for the purposes of process monitoring and control.

BRIEF DESCRIPTION OF THE DRAWINGS

Preferred embodiments of the present invention will now be more particularly described, by way of example only, with reference to the accompanying drawings, in which:

FIG. 13(c) shows 1000 stacked images along section A in FIG. 13(b) where a relatively light ball is falling through;

FIG. 13(d) shows 1000 stacked images along section B in FIG. 13(b) where a relatively heavy ball is falling through;

DESCRIPTION OF THE PREFERRED EMBODIMENTS

Throughout these documents, the following terms are used:

"on-line measurement"—synchronised measuring and imaging on the process line.

"two-phase flow"—a fluid comprising two components, wherein there are differences in the electrical properties of the two components.

"SCG method"—a sensitivity theorem based algorithm using a conjugate grading method.

"back projection method"—a linear approximation algorithm.

"data pipeline processing arrangement"—an arrangement in which each processor (DSP) in the pipeline performs a particular function on the data and then hands over to the next DSP in the pipeline. All of the processors operate on data simultaneously so that data can be processed much more quickly than would be possible with a conventional DSP arrangement.

System Overview

Figure 1:
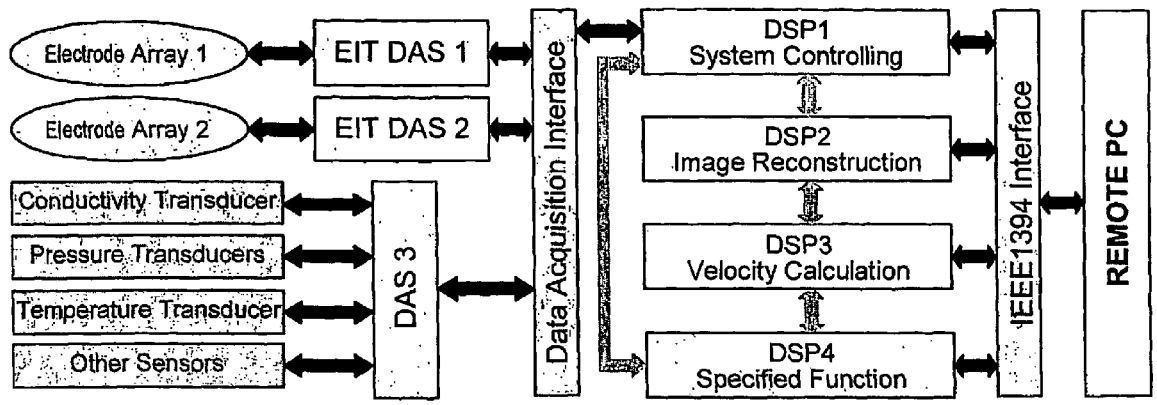
FIG. 1 illustrates the system architecture.

The measurement system, as shown in FIG. 1, includes up to four Digital Signal Processor modules (DSP1-DSP4), two identical Data Acquisition Subsystems (DAS1, DAS2) connected to two electrode arrays (Electrode Array 1, Electrode Array 2), and a third Data Acquisition Subsystem (DAS3) collecting data from conductivity, pressure, temperature and other auxiliary sensors/transducers. AU three DASs are controlled by system-controlling DSP module DSP1 through a common interface (Data Acquisition Interface). Each of DSP1-DSP4 can be configured to communicate one at a time with a remote PC.

All of the DSP modules are preferably identical to reduce the design and debugging tasks. The TMS320C6202B/6713

DSP chip [TI 2000] may be used for the DSP module. Any DSP module can communicate with a remote PC via an IEEE1394 interface, shown in FIG. 1, to make the functionality of the system flexible. The four DSP modules work on a data pipeline processing technique to increase the data-processing speed.

They can perform different tasks on data in the pipeline, for example in the illustrated embodiment, DSP1 controls data acquisition and processes raw data; DSP2 performs image reconstruction, DSP3 fuses the image data to obtain flow information by performing velocity calculations and DSP4 is provided to carry out other specified functions.

Figure 2:
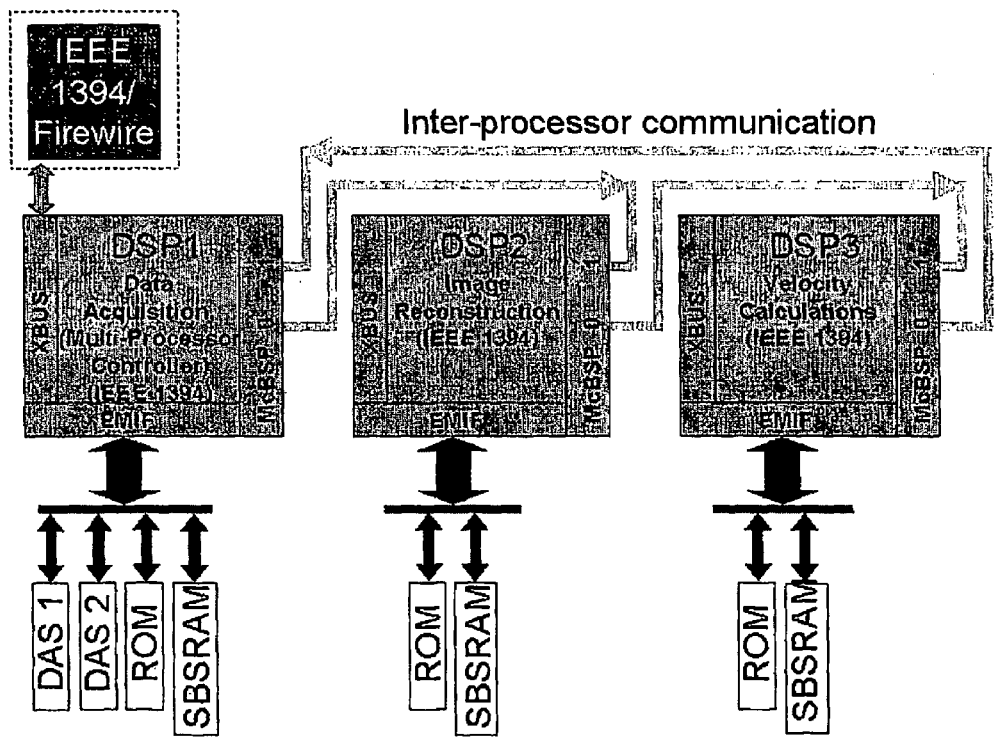
FIG. 2 shows one possible system configuration of a high performance two-phase flow meter using the DSP module as a building block, (a) Single Read-Operation Timing, (b) Single Write-Operation Timing.

FIG. 2 is a block diagram showing how DSP modules are used to implement such a high performance system. DSP1 acts as the system controller and controls the data acquisition process of the three data acquisition subsystems (DAS1-DAS3) which are only connected to DSP1. DSP1 then formats the data and transfers it to DSP2. The data are transmitted via McBSP0 on DSP1 and received via McBSP1 on DSP2. Besides these tasks, DSP1 is also responsible for the IEEE1394 interface communication.

EIT Data Acquisition Subsystems

Figure 3:
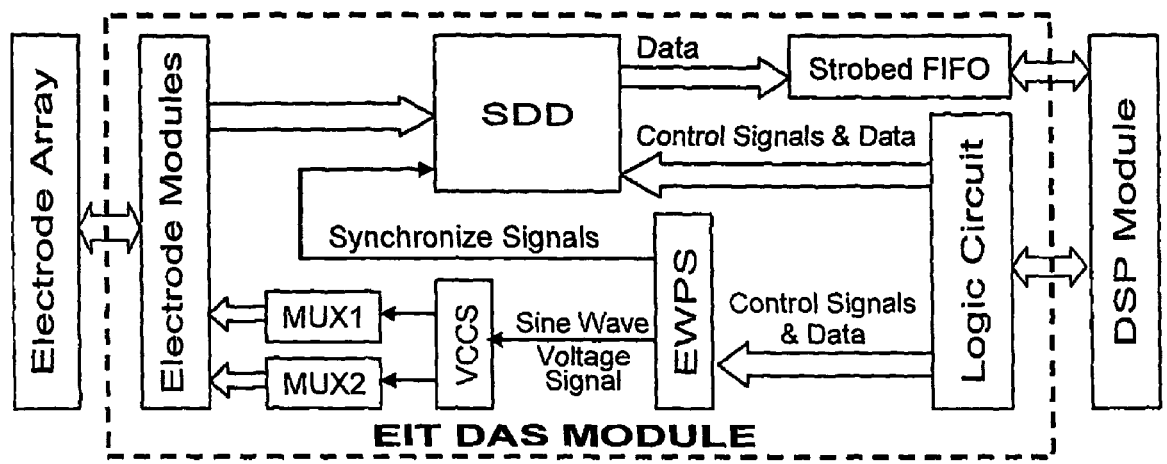
FIG. 3 illustrates the architecture of the EIT data acquisition subsystems (DAS)

Two identical data acquisition subsystems (DAS1, DAS2) are included in the system to collect data from two electrode arrays (a dual-plane sensor). A block diagram of a DAS module is shown inside the dashed-line box in FIG. 3. The four modules of most importance in the DAS module are: a Voltage Controlled Current Source (VCCS), an Equal-Width Pulse Synthesizer (EWPS), a Synchronized Digital Demodulation (SDD) unit and an over-zero switch (OZS) in the control base.

Voltage Controlled Current Source (VCCS)

Figure 4:
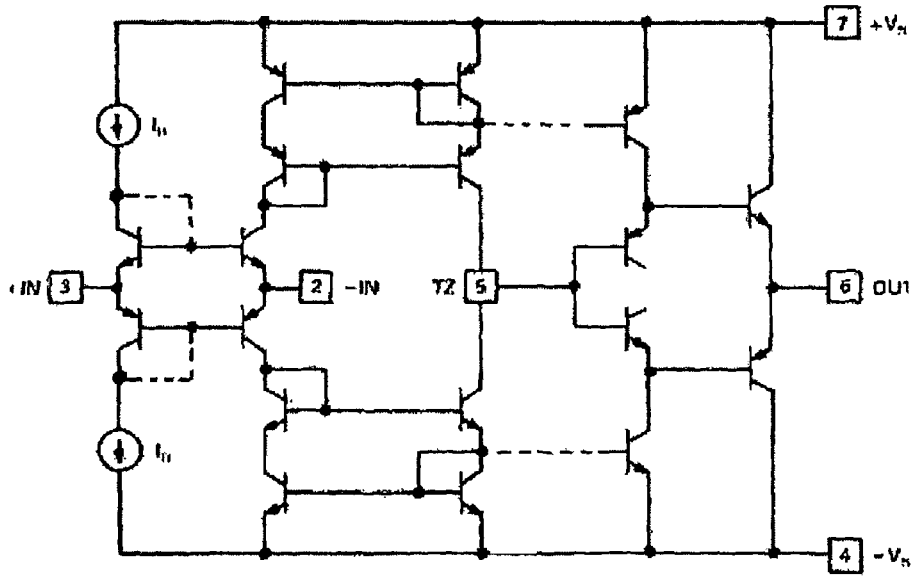
FIG. 4 shows a simplified schematic (a) and an equivalent schematic (b) for AD844.
Figure 4:
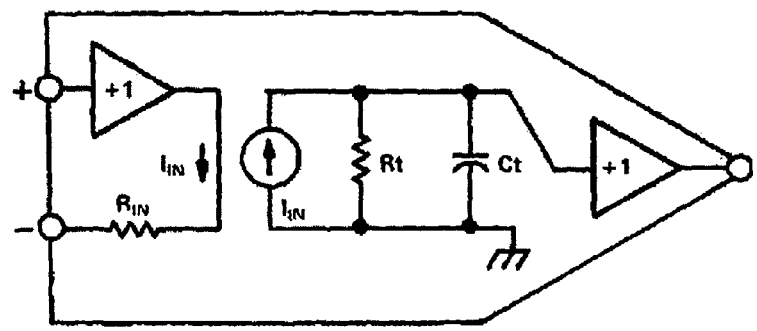

The AD844 from Analogue Devices has a wide bandwidth of 60 MHz and very high output slew rate of up to 2000 V/ms. It differs from a conventional op amp in that the signal inputs have radically different impedances. As schematics shown in FIG. 4, its non-inverting input (Pin 3) presents the unusual high impedance while the inverting input (Pin 2) presents low impedance, $R_{IN}$, of about 50Ω. A current applied to the inverting input is transferred to a complementary pair of wideband unity-gain current mirrors which deliver the same current to an internal slewing (TZ) node (Pin 5). It can be seen that Pin 5 and the inputs behave as a good VCCS with high output impedance and wideband. The one drawback is its small transient current range of ±10 mA in comparison with general ERT requirements. To overcome this problem, a parallel structure consisting of eight AD844s has been developed and shown in FIG. 5.

Two inverse-phased sin-wave voltage inputs are buffered by OPA 602 buffers and then connected to the non-inverting input of each AD844, where two capacitances C connected with the inverting inputs 2 of the OPA 602 buffers and two resistances r connected with the output 6 of a first AD844 chip can perfectly restore the Direct-Current (DC) components generated in the circuit and then cancel the DC offset at the current outputs. Eight AD844s constitute 4 pairs of two-output VCCSs.

Two inverting inputs of each pair of AD844s are connected together with a current setting resistor R. The positive and negative current outputs of each pair are summed together to form larger current outputs. The total output currents can be estimated using the following function:

$$\pm I_{OUT} = \pm 2 \times V_{SIN}/(2 \times R_{IN} + R) \quad \text{(Equation 1)}$$

Figure 5:
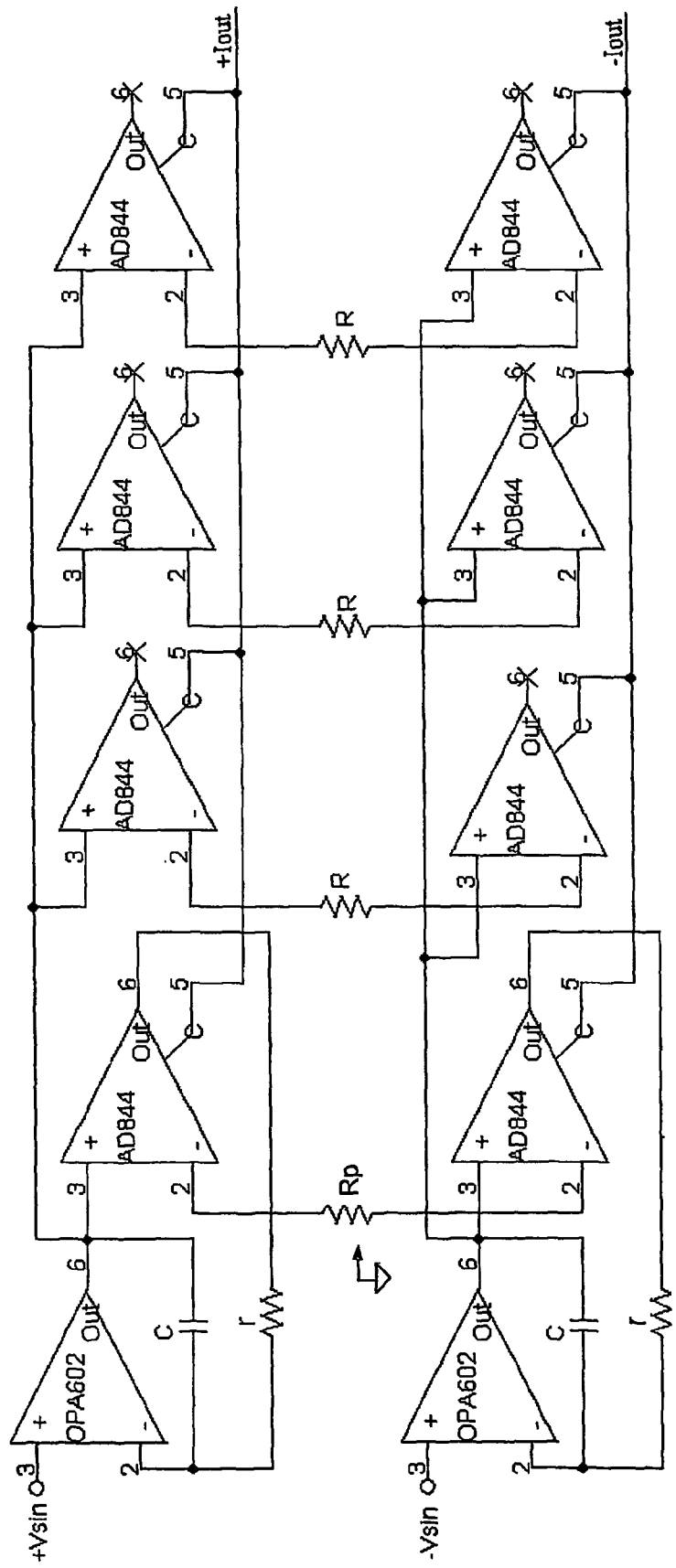
FIG. 5 shows a voltage controlled current source (VCCS)

Compared to other VCCS designs, the advantage of the VCCS shown in FIG. 5 is its excellent balance property. The $\pm I_{out}$ have ideal 180° phase difference and ignorable DC biasing and their amplitudes can be easily balanced with the potentiometer, Rp. The maximum output current amplitude of this circuit is 30 mA. Its output impedance is about 750 kΩ∥18 pF.

Equal-Width Pulse Synthesizer (EWPS)

Figure 6:
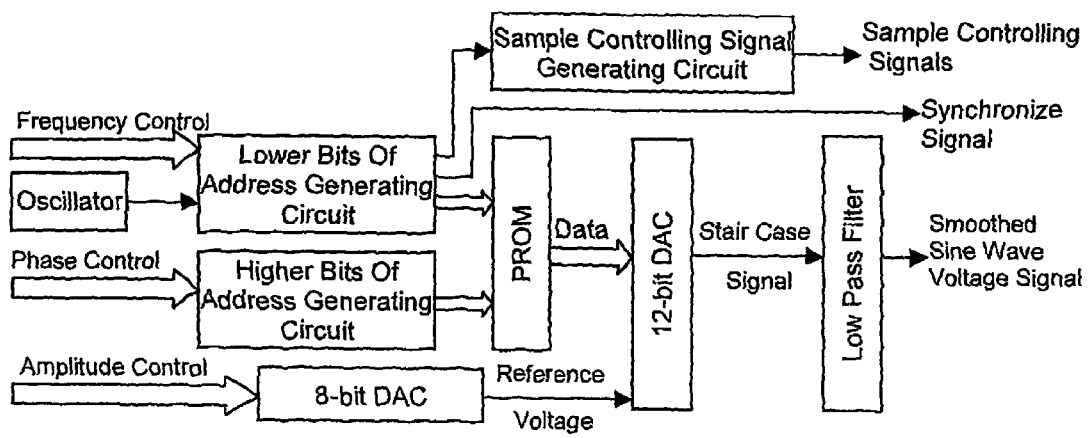
FIG. 6 shows the structure of the Equal-Width Pulse Synthesizer (EWPS)

The EWPS structure, shown in FIG. 6, is similar to that of the widely used Equal-Sample Signal Generator (ESSG). An auto-run clock signal triggers the address generator to continuously output addresses to a pre-programmed memory. The memory then sequentially outputs data to a 12-bit Digital-to-Analogue Converter (DAC). A low-pass filter then smoothes the staircase signal output from the DAC to the required sine-wave voltage signal. The frequency, phase and amplitude of the generated signal can be set by outside controlling unit—DSP.

The difference between EWPS and ESSG is that the former has different sample numbers at different frequencies to make the staircase wave use the same time step-length at all frequencies, while the latter has the same number of samples at all frequencies so the staircase wave has different time step-lengths at different frequencies. This difference has led to a significant reduction in the complexity of the filter design using EWPS as it only needs to set one corner-frequency for the filter for all signal frequencies while the ESSG needs to set different corner-frequencies for the filter for different signal frequencies.

Considering the use of the same step-length, the sampling pulse frequency $f_s$ is unchanged.

$$f_s = Nf_0 \text{ or } f_0 = \frac{1}{N}f_s \quad \text{(Equation 2)}$$

Therefore, $$H(f) = \frac{1}{2T} \sum_{k=-\infty}^{+\infty} \Delta\left[f - \frac{Nk \pm 1}{N}f_s\right] T \text{sinc}\left(\frac{\pi f}{f_s}\right) \quad \text{(Equation 3)}$$

Figure 7:
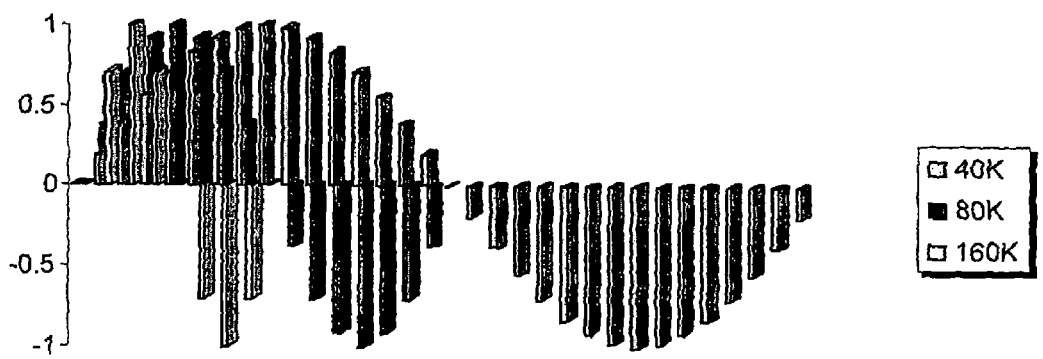
FIG. 7 shows waveforms generated by the EWPS.

Hence, the lowest harmonics from the EWPS is $$\frac{N-1}{N}f_s$$

and the EWPS may use one low pass filter with a fixed corner frequency for all waveforms. The step-length used in the EWPS is 0.5 μs which gives a sampling pulse frequency of 2.0 MHz. The waveforms generated by EWPS are illustrated in FIG. 7.

The specially designed EWPS also provides a convenient way to produce synchronized signals and sample control signals that are necessary in controlling SDD. The synchronous signal (square wave) is used to control the start and the end of the sampling sequences and the sampling pulses are used to actually trigger ADC's conversions at specific times. The timing of both signals and the width of sampling pulses play a very important role in the achievement of SDD accuracy.

Sychronized Digital Demodulator (SDD)

Figure 8:
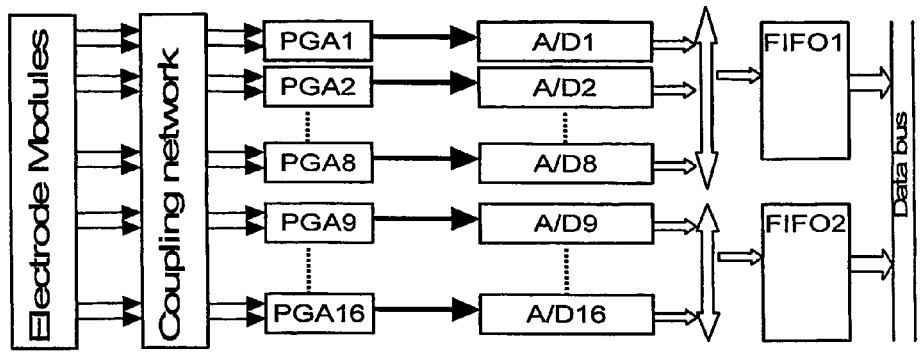
FIG. 8 shows the structure of the Synchronised Digital Demodulation (SDD)

The Synchronized Digital Demodulator (SDD) is a high speed, synchronized parallel digital demodulation system, which is composed of 16 sets of Programmable Gain Amplifiers (PGA) and 12-bit ADC, two sets of Strobed First-In First-Out (FIFO) Memory and control logic. FIG. 8 shows the functional block diagram of the SDD. The sampling pulse signal from EWPS triggers all sixteen ADCs to acquire measurement data in parallel at precisely defined intervals. Two sampling modes are available.

In Mode I, 4, 8, 16, or 32 samples can be selected in one sine wave cycle as the same as the conventional sampling method.

Mode II uses a rolling-sample method. It acquires all samples over several sine-wave periods with one sample per period and a fixed phase shift between one sample pulse and the one after. Sampling Mode II is particularly designed for sampling at a high frequency due to the speed limitation of the ADC.

Figure 9:
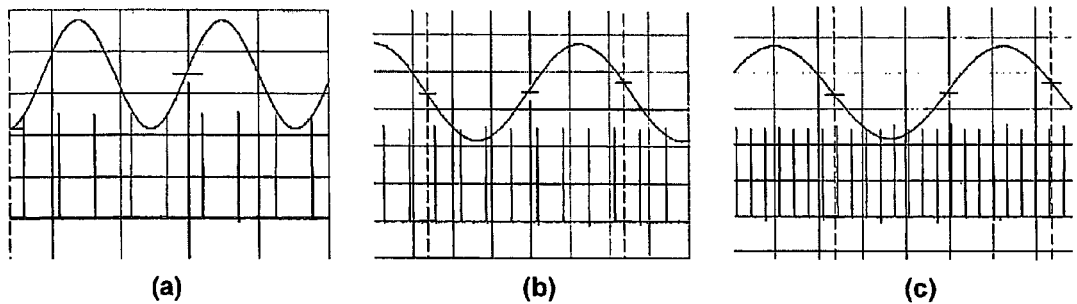
FIG. 9 shows the configuration of the sampling modes, (a) 4 samplings, (b) 8 samplings, (c) 16 samplings, (d) rolling-sample method.
Figure 9:
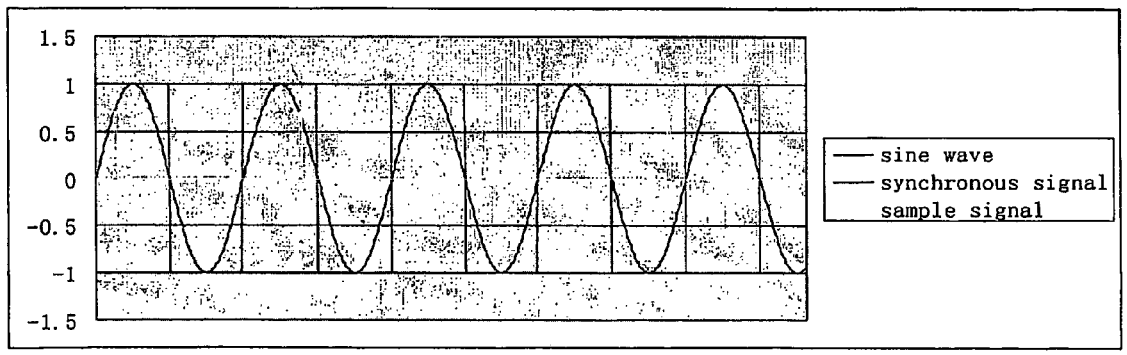

The configuration of the two sampling modes is shown in FIG. 9. The completion signal combined from ADC's conversion status signals will then trigger a control clock to sequentially push converted digital data into two FIFO memories. All operations are fuilly logical controlled without the involvement of the DSP, except the starting signal of each frame of measurement.

Figure 10:
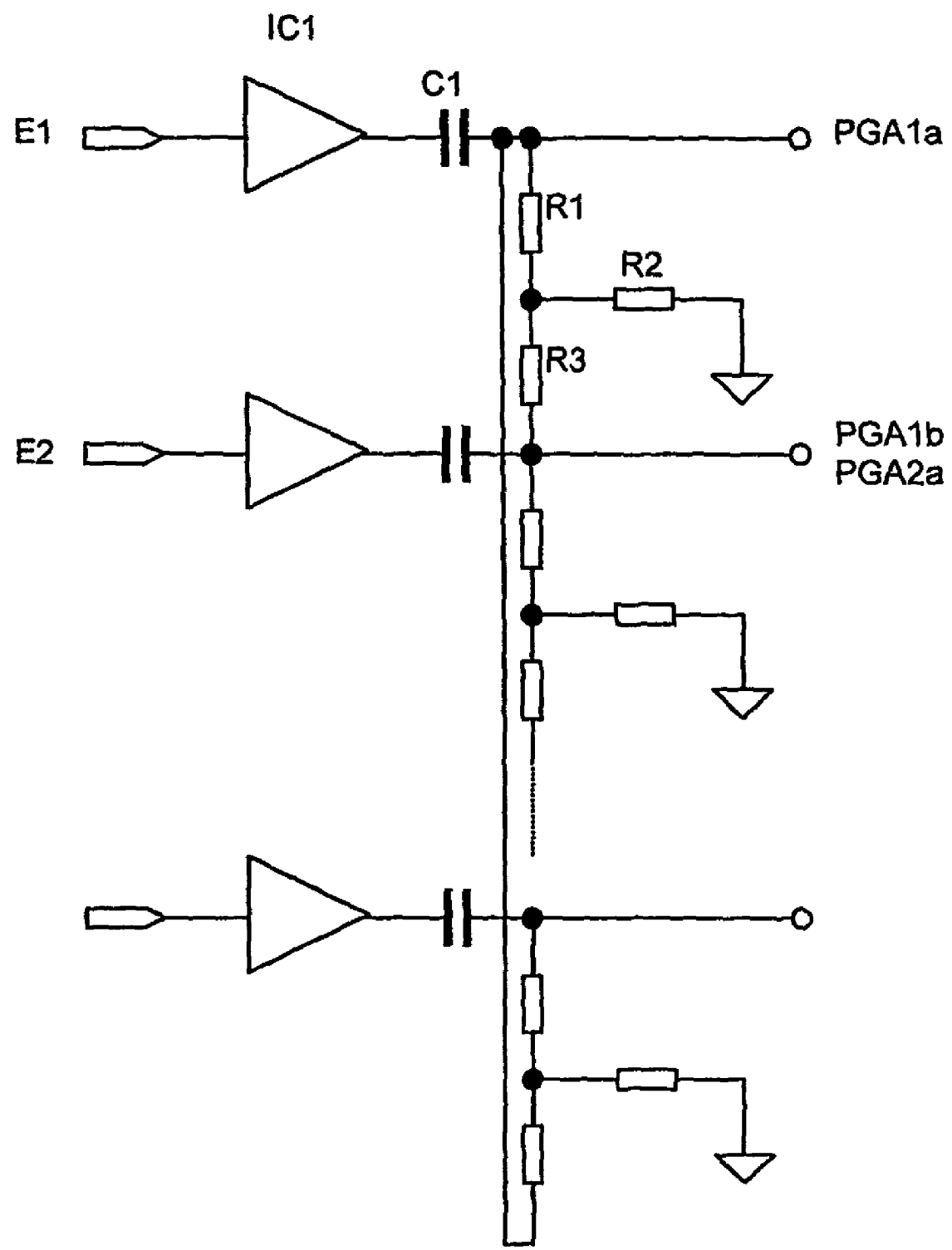
FIG. 10 shows an AC-coupling network.

The coupling circuits, as shown in FIG. 10, are made of a number of voltage buffers IC1 and passive components C1, R1, R2, R3 to provide a wide bandwidth and fast settling ac-coupling interface, as well as a dc bypass to the dc current bias of the programmable gain amplifier (PGA). The input can be configured in either the single or the differential input mode. Only the differential mode is illustrated in FIG. 10 for the use of the adjacent measurement strategy in electrical impedance tomography, where R1=R3 and R1 is much smaller than R2. Therefore, R2, C1 dominate the bandwidth of the coupling, R1 and R3 provide a DC bypass to the DC current offset of PGA but the responding speed is fast since the transient time is dominated by R1 or R3.

Over Zero Switch (OZS)

Conventional ERT systems use sinusoidal current sources to excite the sensing field. Since a controlling unit, such as a PC, DSP or microcomputer, directly controls the current switching between electrodes, the switching operation may occur randomly at any time during a sinusoidal cycle. When the current value at the time of the switching operation is non-zero, electrical charge may reside in the capacitances of the signal passing circuit, such as the double layer capacitance at the electrode-electrolyte interface, the coupling capacitance and the stray capacitance, where the double capacitance plays a major role in all capacitances. These may result in residual potentials presented between these capacitances and produce an additional contribution to next excitation and measurement. These residual charges will require several sinusoidal cycles to die-out, which means the whole data acquisition system (DAS) has to wait for several cycles after each switching operation in order to perform next voltage measurement.

The over-zero switch (OZS) aims to eliminate the charged residual voltage by controlling the switching operation of the current injection. In an ideal case, no charged potential resides in either the double layer capacitance or the coupling capacitance after switching off the current injection so the settling time is shorter with the data acquisition speed being increased. Since the charged voltage has a $\pi/2$ delay with respect to the current, the switch should operated at the time either a zero-voltage presents between the double-layer capacitance or a maximum-current through the capacitance. The current-maximum is actually applied to optimise the switching time or the relevant phase difference between the synchronised signal and the sinusoidal signal, as the charged voltage between the double-layer capacitance is hardly measurable.

Figure 11:
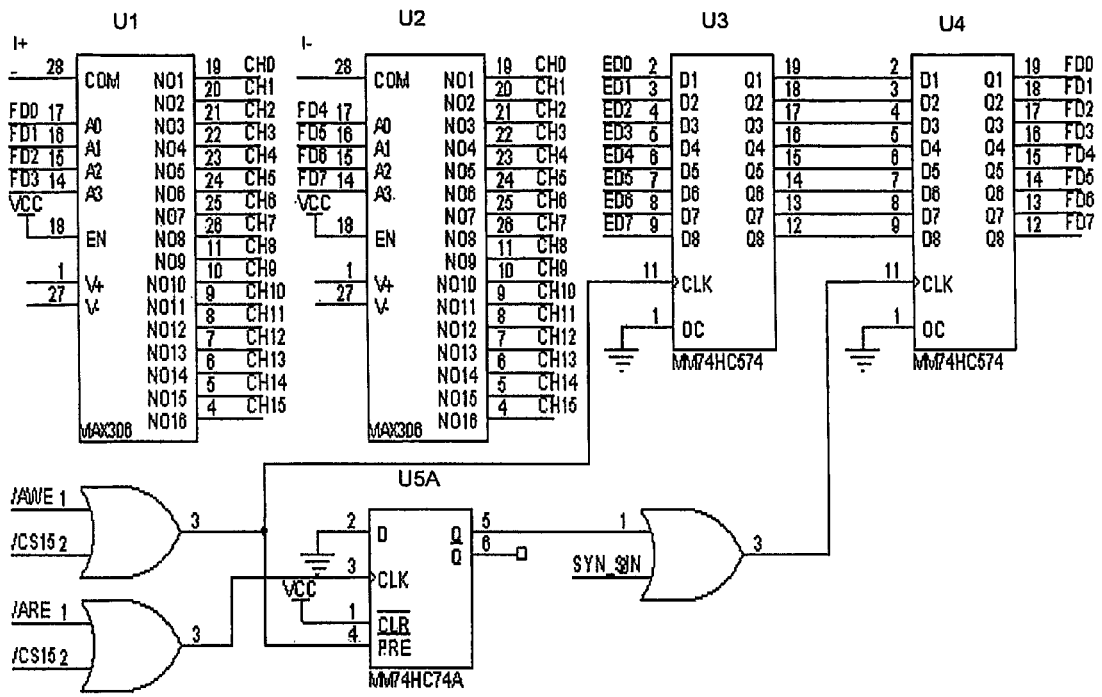
FIG. 11 shows the trigger circuit of the over zero switch (OZS)

FIG. 11 is the circuit used in the improved system to realize the over-current-zero switching technique. Two inverse-phased currents I+ & I– are connected to the common inputs of two multiplexers U1 & U2 respectively. The multiplexers may be MAX306 chips. 16 electrodes mounted in one sensing plane are connected to the 16 output channels (CH[0:15]) of each multiplexer U1,U2. Channel selection is together controlled by DSP command and a synchronize signal, SYN_SIN. SYN_SIN is a square-wave signal, which has the same over-zero point with two current signals I+ & I–. When DSP send out a switching command, an 8-bits data (each multiplexer is controlled by 4-bits data), ED [0:7], is written into the first flip-flop, U3 via inputs D1-D8. This data is later written into the second flip-flop, via outputs Q1-Q8 of U3 into inputs D1-D8 of U4 by the next rising edge of SYN_SIN, and then make the two multiplexers U1,U2 switch to other channels. A D-type flip-flop, U5A, is used in this circuit to prevent writing data into U4 before the data has been set-up at the output of U3. Flip-Flops U3, U4 may be MM74HC574 flip-flops and flip-flop U5 may be a MM74HL574A flip-flop.

Test Results

A laboratory test vessel (a "phantom") fitted with 16 stainless steel electrodes and filled with mains tap water was used in one of the trials. In the experiment, all the PGAs in the SDD were equally set to a fixed gain value in order to simplify the test. The current excitation frequency was 80 kHz. Measurements were taken from all electrodes during each current excitation projection, which gave 256 measurements. Four samples per period were taken. Therefore, each frame data has a total of 1024 measurements. A simplified digital matched-filter was applied to demodulate the data. A set of independent measurements were then extracted and averaged from their mirror data based on the reciprocal theorem.

Figure 12:
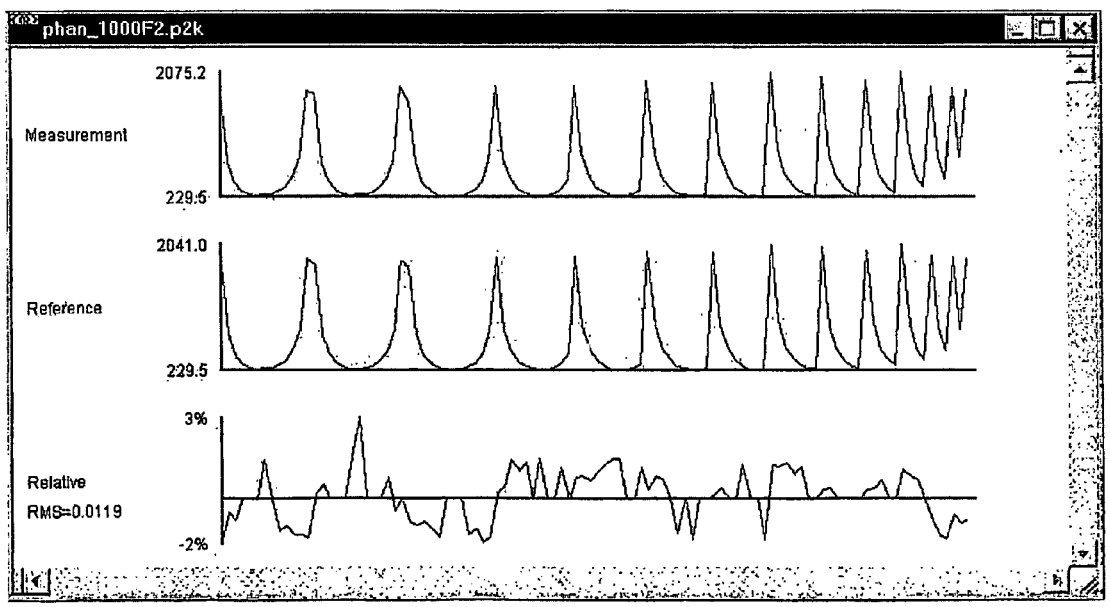
FIG. 12 shows a typical curve of independent measurements obtained from a phantom filled with mains tap water.
Figure 13:
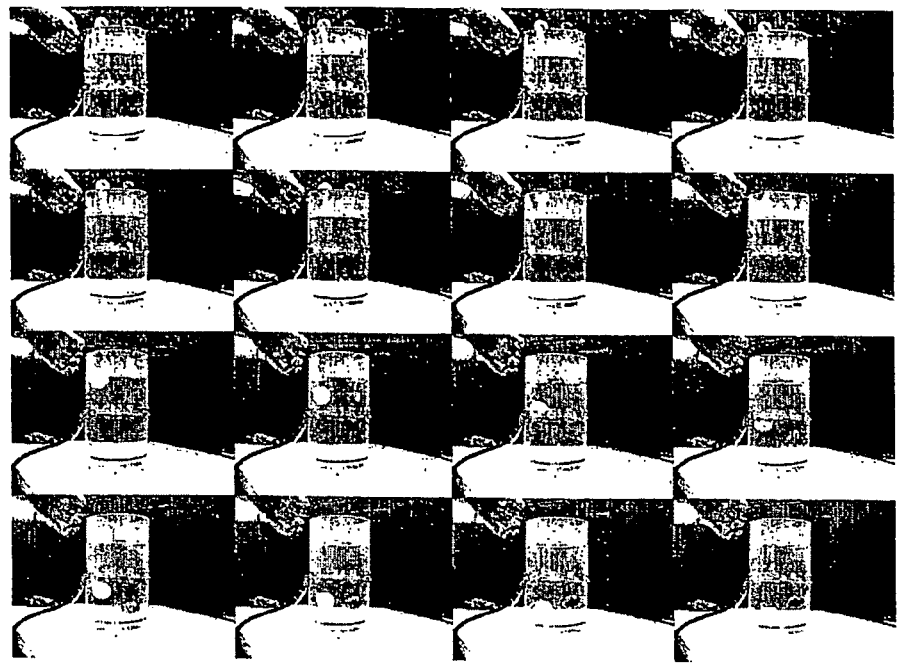
FIG. 13 shows photographs of two balls dropping, one relatively heavy and one relatively light.
Figure 13B:
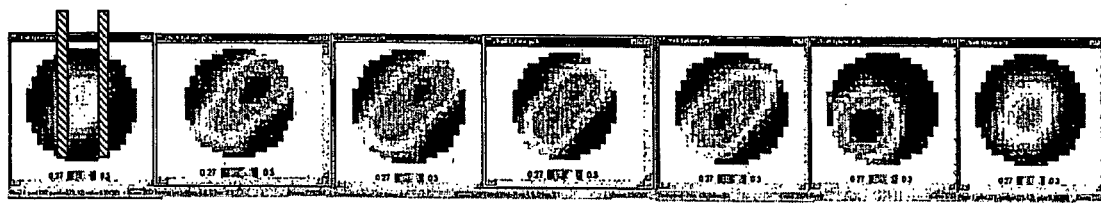
FIG. 13(b) shows 2D EIT images.
Figure 13C:
Figure 13D:
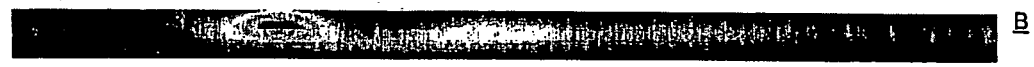
Figure 13E:
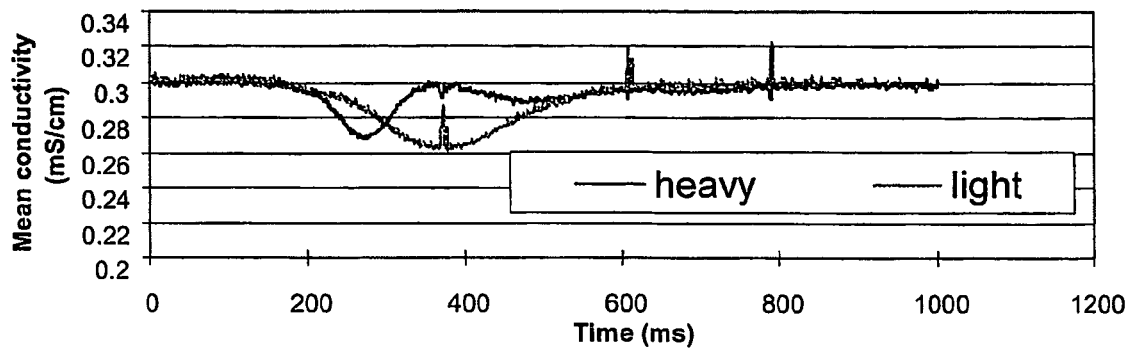
FIG. 13(e) shows the variation of averaged conductivities at the pixels along the sections A and B, according to time elapsed.

The top and middle curves in FIG. 12 present two of measurements obtained from vessel filled with mains tap water. The bottom curve denotes the relative change between the two measurements to reflect the repeatability of these measurements. To demonstrate the high speed of the new EIT system, a test was carried out by dropping two non-conductive balls. The two balls have similar dimensions but different densities (radius, SG and conductivity of the two balls are as follows: R1=1.74 cm, R2=1.75 cm, SG1=2.55, SG2=1.13 and $\sigma_{1,2}$=0). The two balls were dropped to the bottom of the phantom (see FIG. 13), arriving at different times. The time difference can be clearly visualized from the EIT images (FIG. 13b), 1000 stacked EIT images along the sections A and B (FIGS. 13c and 13d) and the reconstructed conductivity changes at relevant pixels as shown in FIG. 13e. The relatively heavy ball dropped in section A arrived at the bottom earlier than the relatively light ball dropped at section B. It can even be seen from both the photographs and EIT images (FIGS. 13d & e) that the heavy ball bounced back when it first knocked the bottom.

The total number of data collection points depends on the sampling rate (the number of samples per signal period). With a fixed sampling rate of 320 kHz, there are 1024 measurement points from one sensing plane with 16 electrodes for one frame image at the signal frequency 80 kHz, or 2.048 million data collection points from a dual-plane sensor for 2000 frames of images at the signal frequency 80 kHz. After the optimization of the controlling unit of DSP C6202 modules at aspects of data collection procedure, memory management, internal data transferring and program coding, the data acquisition speed of the system increases significantly. A data acquisition speed of 1163.6 dual-frames per second (dfps) at 80 kHz (2327.2 frames per second in total) can be achieved. The data acquisition speeds at different signal frequencies are summarized below:

| s.f. (kHz) | 10 | 20 | 40 | 80 | 320 |
|---|---|---|---|---|---|
| Data acquisition speed (d.a.s.) at different signal frequencies (s.f.) d.a.s. (dfps) | 150.0 | 295.4 | 590.8 | 1163.6 | 928.2 |

Data Processing Algorithms

Two image reconstruction algorithms have been coded for the DSP module. They are Sensitivity-map-based Back Projection (SBP) method and a simplified SCG method—Single-step SCG (SSCG) method. The SSCG method is based on the SCG method but only iterated once from a homogenous conductivity distribution. The SBP method is the simplest and fastest. It seems that the SSCG has a better performance than the SBP method.

Data format in floating point is adopted in most cases due to the use of the ill-conditioned sensitivity matrix for image reconstruction. However, a DSP module C6202 with fixed-point data format was used in an earlier version of the system which was relatively slow to process the data in floating-point format. It only can reconstruct images with the SBP method at a speed of 189.0 frames per second, which is much lower than the online data collection speed. Therefore, a floating-point DSP module, C6713 is used in the system of the present invention to obtain a higher image reconstruction speed. This has achieved an image reconstruction rate of 577.4 frames per second.

An online-updating cross-correlation algorithm has been developed Assuming that the two EIT electrode arrays are installed parallel on the flow-pipe, the axial-flow velocity distribution can be estimated by a direct cross-correlation method, as given in Equation 4:

$$R_{12}(n) = \sum_{m=n+1}^{N} f_1(m-n)f_2(m), \quad n = 0, 1, \cdots, (N-1) \quad \text{(Equation 4)}$$

where N is the sample length, and $f_1(m)$ & $f_2(m)$ are the $m^{th}$ up-flow and down-flow images respectively. Eq. 1 can be simply implemented online by updating the $R_{12}(n)$ with the new k-th images, as described in the following:

$$R_{12}^{(k)}(n) = R_{12}^{(k-1)}(n) + f_1(k-n)f_2(k), n=0, 1, \ldots, (N-1) \quad \text{(Equation 5)}$$

where superscript (k) indicates that the corresponding value is of k-th sample. This implementation can greatly save calculation time and reduce memory size. The computation speed is subject to the number of pairs of images that are estimated as a maximum sampling length.

The minimum acquisition time, t, can be taken as twice the product of the minimum transit time of the fluid, τ, and the fractional velocity discrimination, k. Rearrangement gives the following $$k = t/2 \quad \text{(Equation 6)}$$

Therefore, the speed of data collection plays a dominant role in the use of cross-correlation algorithm. If the distance between two sensing planes is d=0.1 m then τ=0.1 m/10 ms$^{-1}$=0.01 s. If f=1000 frames/s was achieved then t=0.001 s. Using Equation 6 gives a discriminatory precision of 0.05 or 5%. The local velocity can be derived from the correlated frame number, n, at each imaging pixel, as given by Equation 7:

$$c = fd/n \quad \text{(Equation 7)}$$

Figure 14A:
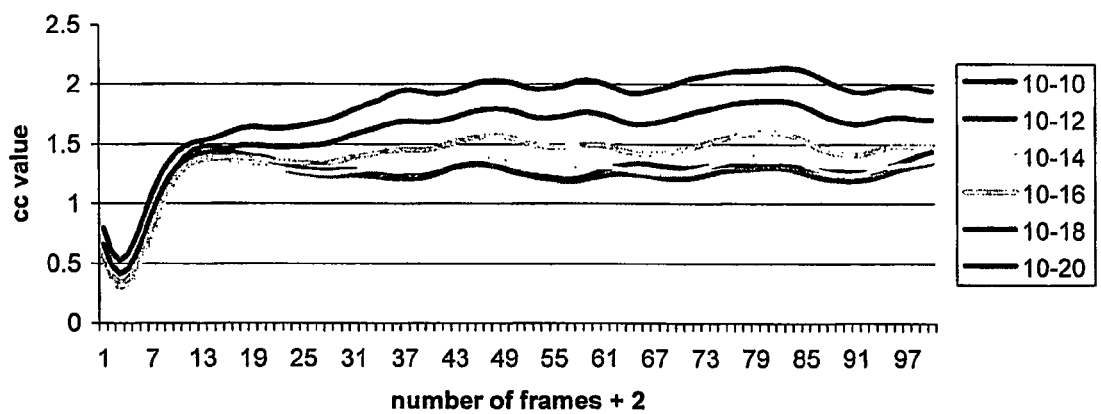
FIG. 14 shows cross-correlation curves at six sampling pixels along the radius of sensing planes via data collection speeds.
Figure 14B:
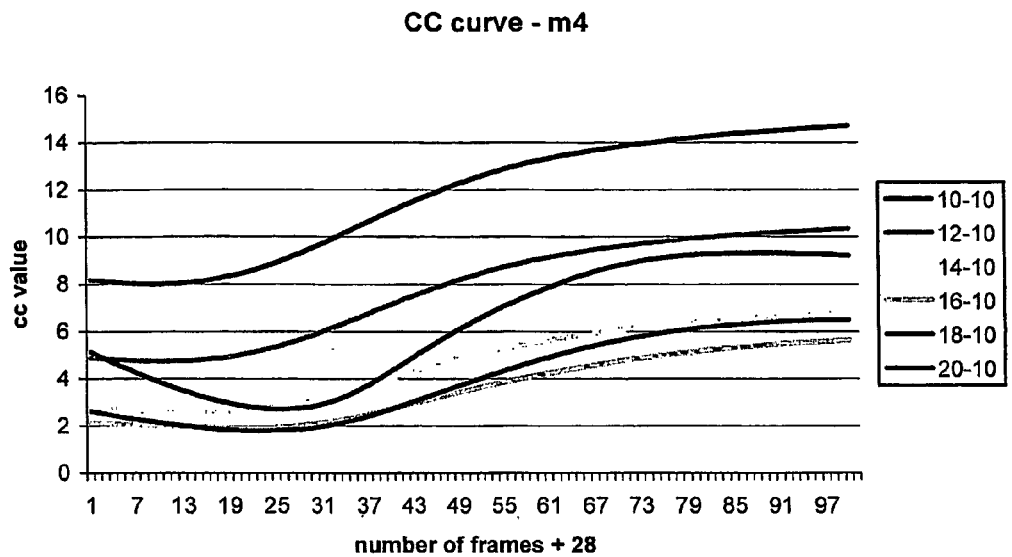
Figure 15:
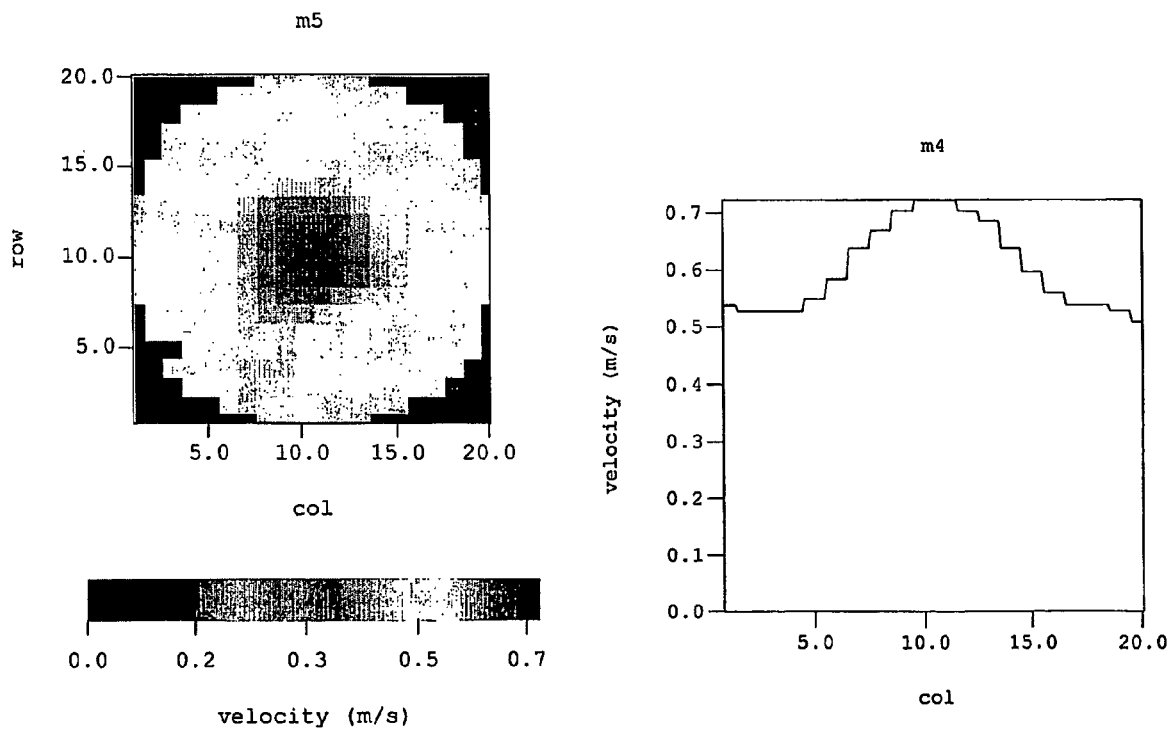
FIG. 15 shows 2D flow velocity profiles from an oil-water axial flow (M4) with superficial velocity: Vwater=0.249 m/s, Voil=0.05 m/s.
Figure 16:
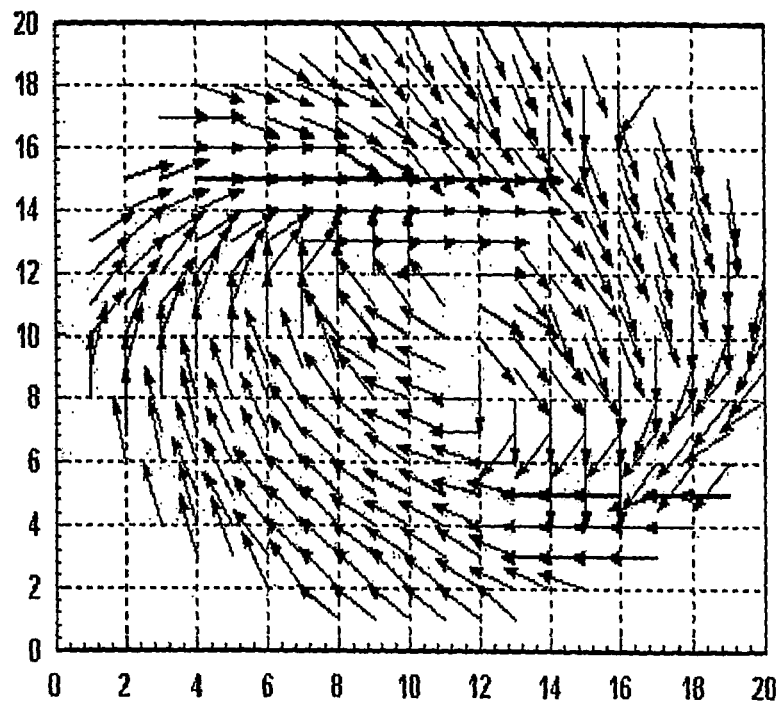
FIG. 16 shows flow velocity profiles from an air-water swirling flow with superficial velocity: Vwater=0.39 m/s, Vgas=0.067 m/s. (a) 2D profile from the combination of angular and radial velocity; (b) 3D profiles from the combination of all 3 dimensional velocity profiles.
Figure 16:
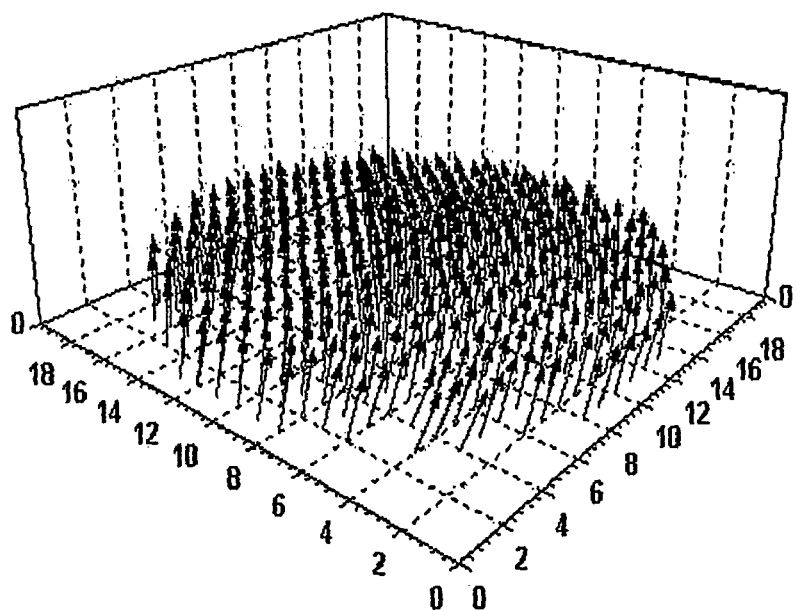

The importance of data collection speed is demonstrated in FIG. 14. The legend numbers are the x- and y-coordinates for a vessel with a diameter 20. Due to the limited data collection speed (FIG. 14a)), the correlated frame numbers (in respect to the lowest cc-value) are small and therefore, they produce a poor resolution in flow velocity measurement. A good resolution from the fast system is clearly illustrated in FIG. 14(b).

The invention claimed is:

1. An electrical impedance tomography (EIT) data processing system, for acquiring and processing data from two-phase flows, comprising a dual-plane sensor, a plurality of digital signal processing modules configured in a data pipeline processing arrangement and a plurality of data acquisition subsystems in communication with a first one of said plurality of digital signal processing modules;
    wherein at least one of the data acquisition subsystems includes an over-zero switch comprising: at least one multiplexer and at least one flip-flop;
    the at least one multiplexer arranged to supply a sinusoidal signal to a selected one of a plurality of channels of the dual-plane sensor according to an output of the at least one flip-flop;
    the at least one flip-flop arranged to receive a synchronization signal that has the same over-zero point as the sinusoidal signal, the synchronization signal causing the at least one flip-flop to output a channel selection signal.

2. The system as claimed in claim 1 wherein said data acquisition subsystems are in communication with a first one of said plurality of digital signal processing modules via a data acquisition interface.

3. The system as claimed in claim 1, wherein the data pipeline processing arrangement is capable of acquiring and/or processing 1000 dual frames per second per dual-plane.

4. The system as claimed in claim 1, wherein said digital signal processing modules are selectively in communication with a remote PC.

5. The system as claimed in claim 1, wherein a first one of said digital signal processing modules is capable of controlling data acquisition and processing.

6. The system as claimed in claim 1, wherein a second one of said plurality of digital signal processing modules is capable of image reconstruction.

7. The system as claimed in claim 1, wherein the plurality of digital signal processing modules comprises four digital processing modules and wherein a third one of said plurality of digital signal processing modules is capable of performing velocity calculations by fusing image data to obtain flow information.

8. The system as claimed in claim 7, wherein a fourth one of said digital signal processing modules is capable of being configured to carry out additional selected functions.

9. The system as claimed in claim 1, further comprising transducers for obtaining conductivity, pressure and/or temperature information, the transducers being in communication with one of said data acquisition subsystems.

10. The system as claimed in claim 1, wherein said dual-plane sensor comprises an electrode array in communication with one of said data acquisition subsystems.

11. The system as claimed in claim 1, wherein said data acquisition subsystems each include a voltage controlled current source, an equal-width pulse synthesiser, and a synchronised digital demodulation unit.

12. The system as claimed in claim 11, wherein said voltage controlled current source comprises a parallel structure of eight AD844 chips configured as four pairs in which the two inverting inputs of each pair are connected together with a current-setting resistor.

13. The system as claimed in claim 12, wherein the four negative current outputs of the four pairs of AD844 chips are summed together to provide a total negative current output.

14. The system as claimed in claim 12, wherein the four positive current outputs of the four pairs of AD844 chips are summed together to provide a total positive current output.

15. The system as claimed in claim 12, wherein the voltage controlled current source further comprises a DC restore facility in which a capacitor and a resistor connected to a non-inverting input of an OPA602 chip, wherein the capacitor is connected to an output of the OPA602 chip and the resistor is connected to an output of a first AD844 chip of the parallel structure, restores DC components generated in the system and cancels a DC offset at the negative and positive current outputs of the AD844 chips.

16. The system as claimed in claim 12, wherein the voltage controlled current source includes a potentiometer for amplitude balancing.

17. The system as claimed in claim 11, wherein said equal-width pulse synthesiser comprises a clock signal for triggering an address generator to continuously output addresses to a pre-programmed memory, the memory output being connected to a digital to analogue converter, the digital to analogue converter providing a staircase signal output, wherein the equal-width pulse synthsiser has different sampling rates at different signal frequencies so that the staircase signal output has the same time step-length at all frequencies.

18. The system as claimed in claim 17 wherein said equal-width pulse synthesiser further comprises a low pass filter connected to the output of the digital to analogue converter to provide a smoothed signal output.

19. The A system as claimed in claim 11, wherein said synchronised digital demodulation unit comprises 16 programmable gain amplifiers each having an analogue to digital converter, two strobed First-In First-Out (FIFO) memories and control logic.

20. The system as claimed in claim 19, wherein the signal output of the equal-width pulse synthesiser triggers said 16 analogue to digital converters to acquire measurement data in parallel at predefined intervals.

21. The system as claimed in claim 11, wherein said over-zero switch comprises two multiplexers, each having 16 electrodes mounted in one sensing plane connected to their 16 output channels and two flip-flops controlled by a switching command from one of said DSP modules.

22. The system as claimed in claim 1, wherein said over-zero switch further comprises a D-type flip-flop.

23. A method of processing electrical impedance tomography comprising:
    a) providing a system as claimed in claim 1; and
    b) processing electrical impedance tomography data for a two phase flow.

24. A non-transitory recording medium having recorded thereon computer implementable instructions for performing the method of claim 23.

* * * * *